US00PP18472P3

(12) United States Plant Patent
Meilland

(10) Patent No.: US PP18,472 P3
(45) Date of Patent: Feb. 5, 2008

(54) HYBRID TEA ROSE PLANT NAMED 'MEIGOUDEA'

(50) Latin Name: *Rosa hybrida*
Varietal Denomination: Meigoudea

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/475,211

(22) Filed: Jun. 27, 2006

(65) Prior Publication Data

US 2007/0300334 P1 Dec. 27, 2007

(51) Int. Cl.
*A01H 5/00* (2006.01)

(52) U.S. Cl. ..... Plt./137

(58) Field of Classification Search ..... Plt./137
See application file for complete search history.

*Primary Examiner*—Kent Bell
*Assistant Examiner*—S. B. McCormick-Ewoldt
(74) *Attorney, Agent, or Firm*—Buchanan Ingersoll & Rooney PC

(57) ABSTRACT

A new and distinct Hybrid Tea rose plant is provided which abundantly forms attractive mildly fragrant very double blossoms that are coral pink in coloration. The growth habit is tall and bushy. Vigorous dense dark green semi-glossy foliage is displayed that contrasts well with the coral pink blossom coloration. The plant is particularly well suited for providing attractive ornamentation in the landscape.

1 Drawing Sheet

Botanical/commercial classification: *Rosa hybrida*/Hybrid Tea Rose Plant.
Varietal denomination: cv. Meigoudea.

SUMMARY OF THE INVENTION

The new Hybrid Tea rose plant was created by artificial pollination wherein two parents were crossed which previously had been studied in the hope that they would contribute the desired characteristics. The female parent (i.e., the seed parent) of the new variety was the product of the controlled cross of the 'Emily Post' variety (U.S. Plant Pat. No. 3,749) and the 'Korlift' variety (non-patented in the United States). The 'Emily Post' variety sometimes is known as the 'Omega' variety and the 'Korlift' variety sometimes is known as the 'Sylvia' variety. The male parent (i.e., the pollen parent) was the product of the controlled cross of the 'Merkor' variety (U.S. Plant Pat. No. 3,724) and the 'Prima Ballerina' variety (non-patented in the United States). The parentage of the new variety can be summarized as follows:

('Emily Post'×'Korlift')×('Merkor'×'Prima Ballerina').

The seeds resulting from the pollination were sown and small plants were obtained which were physically and biologically different from each other. Selective study resulted in the identification of a single plant of the new variety.

It was found that the Hybrid Tea new rose plant of the present invention displays the following combination of characteristics:

(a) exhibits a tall and bushy growth habit, (b) abundantly forms attractive mildly fragrant very double blossoms that are coral pink in coloration, (c) forms vigorous dense dark green semi-glossy foliage that contrasts well with the coral pink blossom coloration, and (d) is particularly well suited for providing attractive ornamentation in the landscape.

The new variety well meets the needs of the horticultural industry and can be grown to advantage in parks and gardens where attractive ornamentation is desired. Good tolerance with respect to Powdery Mildew and Black Spot has been observed.

The new variety of the present invention readily can be readily distinguished from its ancestors. For instance, the 'Emily Post' variety displays soft medium pink strongly fragrant flowers. The flowers of the 'Korlift' variety are pink with a high center and are not fully double. The flowers of the 'Merkor' variety are orange-red in coloration and the blooms of the 'Prima Ballerina' variety are hot pink in coloration with a high center.

The new variety of the present invention also can be readily distinguished from other similar Hybrid Tea varieties such as the 'Meisocrat' variety (U.S. Plant Pat. No. 9,613) and the 'Meikarouz' variety (U.S. Plant Pat. No. 14,039). The blooms of the 'Meisocrat' variety are true pink in coloration, and those of the 'Meikarouz' variety are deep red in coloration.

The new variety has been found to undergo asexual propagation in the South of France and at Wasco, Calif., U.S.A., by a number of routes, including budding, grafting, and by the use of cuttings. Asexual propagation by the above-mentioned techniques at such locations has shown that the characteristics of the new variety are firmly fixed and are stably transmitted by such asexual propagation from one generation to another. Accordingly, the new variety asexually reproduces in a true to type manner.

The new variety has been named 'Meigoudea'.

BRIEF DESCRIPTION OF THE PHOTOGRAPH

The accompanying photograph shows, as nearly true as it is reasonably possible to make the same in a color illustration of this character, a typical specimen of the new variety. The rose plant of the new variety was approximately two years of age and was photographed during June while growing outdoors on *Rosa froebelli* understock near West Grove, Pa., U.S.A.

FIG. 1 illustrates the typical very double coral pink flowers, buds, and dark green semi-glossy foliage of the new variety.

DETAILED DESCRIPTION

The chart used in the identification of the colors is that of The Royal Horticultural Society (R.H.S. Colour Chart), London, England. The description is based on the observation of two-year-old plants during June while growing outdoors on *Rosa froebelli* understock near West Grove, Pa., U.S.A. Color information in common terms sometimes is provided. Such terminology is to be accorded its ordinary dictionary significance.

Class: Hybrid tea.

Plant:

*Height.*—Approximately 130 to 140 cm on average at the end of the growing season.

*Width.*—Approximately 60 to 80 cm at the end of the growing season.

*Habit.*—Tall and bushy.

Branches:

*Young stems.*—Near Green Group 137A in coloration.

*Adult wood.*—Near Yellow-Green Group 146A in coloration.

*Thorns.*—Configuration: slightly concave on the under surface. Size: large, and commonly measure approximately 5 mm in length and approximately 2 mm in width. Quantity: moderately numerous. Color: near Greyed-Yellow Group 162A at the base and near Greyed-Orange Group 164A at the tip.

Leaves:

*General appearance.*—Very dense, dark green, and semi-glossy.

*Petioles.*—Upper surface: near Green Group 137A with some reddish-brown anthocyanin coloration. Under surface: near Yellow-Green Group 146B.

*Stipules.*—General appearance: adnate, pectinate and narrow.

*Leaflets.*—Number: 3, 5 (most often), and 7. Arrangement: alternate and odd pinnately compound. Shape: elliptic-ovate. Apex: generally symmetrical broad point. Base: generally symmetrical and obtuse. Margin: Serrulate and regular. Texture: consistent and rather firm. Color (young foliage): Upper surface: near Yellow-Green Group 147A with large amounts of anthocyanin coloration of Greyed-Red Group 178A. Under surface: near Yellow-Green Group 146A with some anthocyanin coloration of Greyed-Red Group 178A. Color (adult foliage): Upper surface: near Green Group 139A. Under surface: near Yellow-Green Group 146A.

Inflorescence:

*Number of flowers.*—Typically approximately 1 to 5 per stem.

*Peduncle.*—Medium in size, approximately 4.5 to 5 cm in length, and near Yellow-Green Group 146B in coloration with strong anthocyanin coloration approaching Greyed-Orange Group 175D.

*Sepals.*—Number: 5. Shape: elongated and commonly lacking extensions. Texture: tomentose and glandular. Color (upper surface): near Greyed-Green Group 194B. Color (under surface): near Yellow-Green Group 146B with slight anthocyanin coloration that approaches Greyed-Orange Group 166A.

*Buds.*—Shape: ovoid. Size: large. Length: approximately 2 cm on average. Width: approximately 8 mm on average at the widest point. Color: Upper surface: Coral Pink, near Red-Purple Group 62A. Under surface: Coral Pink, near Red-Purple Group 62D.

*Flower.*—Shape: very double and cup-shaped. Diameter: approximately 11 to 12 cm on average when fully open. Flowering stem length: commonly approximately 60 to 70 cm on average. Color (when opening begins): Upper surface: Coral Pink, near Red-Purple Group 62A. Under surface: Coral Pink, near Red-Purple Group 62A. Color (in course of opening): Upper surface: Coral Pink, near Red-Purple Group 62A. Under surface: Coral Pink, near Red-Purple Group 62D. Color (at end of blooming): Upper surface: Coral Pink, near Red-Purple Group 62A. Lower surface: Coral Pink, near Red-Purple Group 62D. Fragrance: Slight. Petal number: commonly approximately 65 to 80 on average. Petal shape: external petals are slightly cordate. Petal size: the petal length commonly is approximately 45 mm on average, and the petal width commonly is approximately 38 mm on average. Petal base: pointed wedge-shaped. Petal apex: rounded and slightly reflexed. Petaloids: none observed during observations to date. Lastingness: very long, the blossoms commonly last approximately 12 days on the plant. The lastingness when cut and placed in a vase has not been evaluated since the variety is primarily intended for providing ornamentation in the landscape. Anthers: near Yellow-Group 11D in coloration. Stamen number: approximately 65 on average. Filaments: near Yellow Group 11D in coloration. Pollen: present in a moderate quantity and near Yellow-Orange Group 14D in coloration. Pistil number: approximately 97 on average. Stigmas: near Red Group 47C in coloration. Styles; near Yellow Group 11D in coloration. Petal drop: the petals commonly detach cleanly before drying. Receptacle: funnel-shaped in longitudinal section and near Yellow-Green Group 146B in coloration. Hips: none observed.

Development:

*Vegetation.*—Very vigorous and strong.

*Blooming.*—Very abundant.

*Aptitude to bear fruit.*—None observed.

*Tolerance to diseases.*—Generally good with respect to Powdery Mildew and Black Spot.

Plants of the 'Meigoudea' variety have not been observed under all possible environmental conditions to date. Accordingly, it is possible that the phenotypic expression may vary somewhat with changes in light intensity and duration, cultural practices, and other environmental conditions without variance in the genotype.

I claim:

1. A new and distinct Hybrid Tea rose plant having the following combination of characteristics:

(a) exhibits a tall and bushy growth habit, (b) abundantly forms attractive mildly fragrant very double blossoms that are coral pink in coloration, (c) forms vigorous dense dark green semi-glossy foliage that contrasts well with the coral pink blossom coloration, and (d) is particularly well suited for providing attractive ornamentation in the landscape;

substantially as illustrated and described.

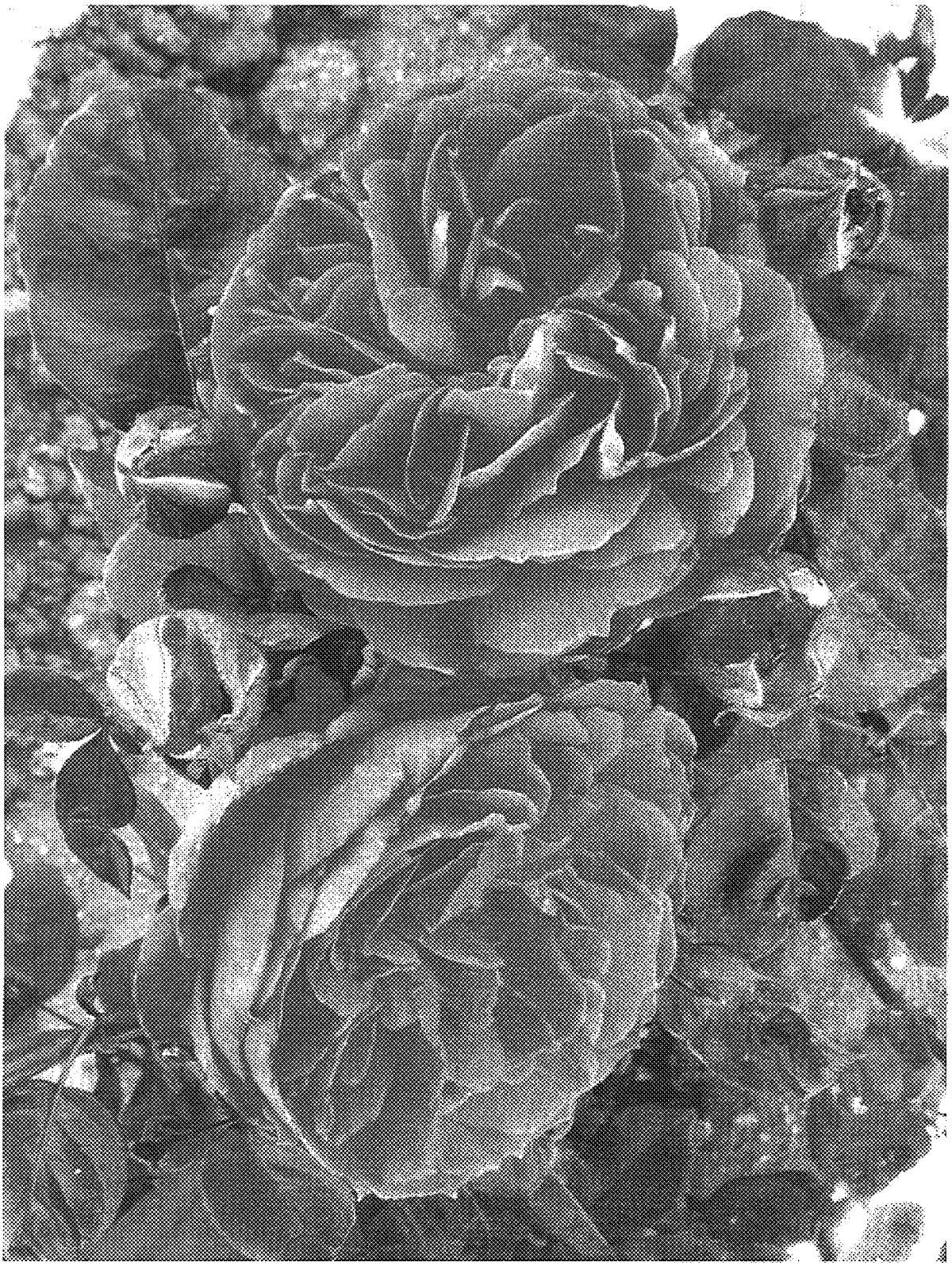

* * * * *